United States Patent
Svensby et al.

(10) Patent No.: US 9,039,668 B2
(45) Date of Patent: May 26, 2015

(54) BODY ATTACHMENT WAFER FOR AN OSTOMY DEVICE

(75) Inventors: Anna Svensby, Västra Frölunda (SE); Päranders Wärja, Hindås (SE); Sofia Lundgren, Göteborg (SE)

(73) Assignee: MÖLNLYCKE HEALTH CARE AB, Göteborg (SE)

( * ) Notice: Subject to any disclaimer, the term of this patent is extended or adjusted under 35 U.S.C. 154(b) by 158 days.

(21) Appl. No.: 13/640,659

(22) PCT Filed: Apr. 12, 2011

(86) PCT No.: PCT/SE2011/000067
§ 371 (c)(1),
(2), (4) Date: Dec. 21, 2012

(87) PCT Pub. No.: WO2011/129738
PCT Pub. Date: Oct. 20, 2011

(65) Prior Publication Data
US 2013/0096522 A1      Apr. 18, 2013

Related U.S. Application Data

(60) Provisional application No. 61/322,971, filed on Apr. 12, 2010.

(30) Foreign Application Priority Data

Apr. 12, 2010   (SE) .................................... 1050354-8

(51) Int. Cl.
*A61F 5/443*   (2006.01)
*A61F 5/44*    (2006.01)
(Continued)

(52) U.S. Cl.
CPC . *A61F 5/443* (2013.01); *A61F 5/44* (2013.01); *A61F 5/448* (2013.01); *A61F 5/445* (2013.01)

(58) Field of Classification Search
CPC ........... A61F 5/44; A61F 5/443; A61F 5/445; A61F 5/448; A61F 2005/445
See application file for complete search history.

(56) References Cited

U.S. PATENT DOCUMENTS 3,878,847 A    4/1975   Marsan ......................... 128/283
4,681,574 A    7/1987   Eastman ....................... 604/344
(Continued)

FOREIGN PATENT DOCUMENTS

CN     102753122      10/2012
EP       0300620   *   1/1989
(Continued)

OTHER PUBLICATIONS

International Preliminary Report on Patentability issued on Oct. 16, 2012 for International Patent Application No. PCT/SE2011/000067, which was filed on Apr. 12, 2011 [Inventor—Svensby; Applicant—Mölnlycke Health Care AB] [6 pages].

(Continued)

*Primary Examiner* — Adam Marcetich
(74) *Attorney, Agent, or Firm* — Ballard Spahr LLP

(57) ABSTRACT

Provided is a body attachment wafer for attaching an ostomy device to a wearer. The body attachment wafer includes a plastic film having an opening therein, a layer of adhesive coated onto one side of the plastic film, and a stiffening layer releasably attached to the plastic film on the side thereof opposite to the side coated with adhesive. The layer of adhesive comprises a region surrounding the opening in the plastic film in which the thickness of the layer of adhesive is decreasing in a direction towards the circumference of the plastic film, the layer of adhesive having its largest thickness adjacent to the opening in the plastic film. The adhesive consists of a silicone gel adhesive having a softness exceeding 8 mm.

8 Claims, 1 Drawing Sheet

(51) Int. Cl.
*A61F 5/448* (2006.01)
*A61F 5/445* (2006.01)

(56) References Cited

U.S. PATENT DOCUMENTS

| | | | | |
|---|---|---|---|---|
| 4,867,748 | A * | 9/1989 | Samuelsen | 604/336 |
| 5,000,748 | A * | 3/1991 | Fenton | 604/340 |
| 5,106,629 | A * | 4/1992 | Cartmell et al. | 424/445 |
| 5,429,625 | A * | 7/1995 | Holmberg | 604/338 |
| 5,520,629 | A * | 5/1996 | Heinecke et al. | 602/57 |
| 5,593,397 | A * | 1/1997 | La Gro | 604/355 |
| 5,722,965 | A * | 3/1998 | Kuczynski | 604/344 |
| 6,106,507 | A * | 8/2000 | Botten et al. | 604/338 |
| 6,197,010 | B1 * | 3/2001 | Leise et al. | 604/338 |
| 6,332,879 | B1 | 12/2001 | Nielsen et al. | 604/344 |
| 6,520,943 | B1 | 2/2003 | Wagner | 604/332 |
| 2003/0073965 | A1 * | 4/2003 | Leise et al. | 604/336 |
| 2004/0106908 | A1 * | 6/2004 | Leise et al. | 604/332 |
| 2006/0276763 | A1 * | 12/2006 | Keyes | 604/339 |
| 2007/0027434 | A1 * | 2/2007 | Pedersen et al. | 604/333 |
| 2007/0106195 | A1 * | 5/2007 | Marcoux et al. | 602/57 |
| 2008/0009779 | A1 | 1/2008 | Fabo et al. | 604/338 |
| 2009/0312685 | A1 * | 12/2009 | Olsen et al. | 602/54 |
| 2010/0114044 | A1 * | 5/2010 | Cramer et al. | 604/332 |
| 2010/0204664 | A1 * | 8/2010 | Bach et al. | 604/344 |
| 2010/0307513 | A1 | 12/2010 | Svensby et al. | 602/54 |
| 2010/0318013 | A1 * | 12/2010 | Fabo et al. | 602/54 |
| 2012/0323193 | A1 | 12/2012 | Johannison et al. | 604/344 |

FOREIGN PATENT DOCUMENTS

| | | |
|---|---|---|
| EP | 0832626 | 4/1998 |
| EP | 1163892 A2 | 12/2001 |
| EP | 1413268 | 4/2004 |
| GB | 1280631 A * | 5/1985 |
| WO | WO 2004/108175 | 12/2004 |
| WO | WO 2006/075948 | 7/2006 |
| WO | WO 2006/075949 | 7/2006 |
| WO | WO 2006/075950 | 7/2006 |
| WO | WO 2009/006902 | 1/2009 |
| WO | WO 2011/129738 | 10/2011 |

OTHER PUBLICATIONS

Written Opinion issued on Jul. 21, 2011 for International Patent Application No. PCT/SE2011/000067, which was filed on Apr. 12, 2011 [Inventor—Svensby; Applicant—Mölnlycke Health Care AB] [5 pages].
International Search Report issued on Jul. 21, 2011 for International Patent Application No. PCT/SE2011/000067, which was filed on Apr. 12, 2011 [Inventor—Svensby; Applicant—Mölnlycke Health Care AB] [6 pages].
Notice of Allowance issued on Oct. 3, 2012 for U.S. Appl. No. 11/794,986, filed Sep. 11, 2007 [Inventor—Fabo; Applicant—Mölnlycke Health Care AB] [10 pages].
Response to Office Action filed on Sep. 14, 2011 for U.S. Appl. No. 11/794,986, filed Sep. 11, 2007 [Inventor—Fabo; Applicant—Mölnlycke Health Care AB] [9 pages].
Final Rejection issued on Mar. 14, 2011 for U.S. Appl. No. 11/794,986, filed Sep. 11, 2007 [Inventor—Fabo; Applicant—Mölnlycke Health Care AB] [12 pages].
Examiner's Interview Summary issued on Jan. 27, 2011 for U.S. Appl. No. 11/794,986, filed Sep. 11, 2007 [Inventor—Fabo; Applicant—Mölnlycke Health Care AB] [4 pages].
Response to Non-Final Rejection filed on Jan. 27, 2011 for U.S. Appl. No. 11/794,986, filed Sep. 11, 2007 [Inventor—Fabo; Applicant—Mölnlycke Health Care AB] [9 pages].
Non-Final Rejection issued on Jul. 27, 2010 for U.S. Appl. No. 11/794,986, filed Sep. 11, 2007 [Inventor—Fabo; Applicant—Mölnlycke Health Care AB] [11 pages].
Examiner's Interview Summary issued on Jul. 23, 2010 for U.S. Appl. No. 11/794,986, filed Sep. 11, 2007 [Inventor—Fabo; Applicant—Mölnlycke Health Care AB] [4 pages].
Response to Final Rejection filed on Jul. 15, 2010 for U.S. Appl. No. 11/794,986, filed Sep. 11, 2007 [Inventor—Fabo; Applicant—Mölnlycke Health Care AB] [11 pages].
Final Rejection issued on Apr. 15, 2010 for U.S. Appl. No. 11/794,986, filed Sep. 11, 2007 [Inventor—Fabo; Applicant—Mölnlycke Health Care AB] [13 pages].
Response to Notice of Non-Compliant Amendment filed on Apr. 5, 2010 for U.S. Appl. No. 11/794,986, filed Sep. 11, 2007 [Inventor—Fabo; Applicant—Mölnlycke Health Care AB] [7 pages].
Notice of Non-Compliant Amendment issued on Mar. 25, 2010 for U.S. Appl. No. 11/794,986, filed Sep. 11, 2007 [Inventor—Fabo; Applicant—Mölnlycke Health Care AB] [3 pages].
Supplemental Response filed on Mar. 9, 2010 for U.S. Appl. No. 11/794,986, filed Sep. 11, 2007 [Inventor—Fabo; Applicant—Mölnlycke Health Care AB] [4 pages].
Response to Non-Final Rejection filed on Feb. 22, 2010 for U.S. Appl. No. 11/794,986, filed Sep. 11, 2007 [Inventor—Fabo; Applicant—Mölnlycke Health Care AB] [14 pages].
Non-Final Rejection issued on Nov. 20, 2009 for U.S. Appl. No. 11/794,986, filed Sep. 11, 2007 [Inventor—Fabo; Applicant—Mölnlycke Health Care AB] [11 pages].
Preliminary Amendment filed on Jul. 10, 2007 for U.S. Appl. No. 11/794,986, filed Sep. 11, 2007 [Inventor—Fabo; Applicant—Mölnlycke Health Care AB] [6 pages].
Response to Final Office Action filed on Dec. 6, 2012 for U.S. Appl. No. 12/671,781, filed Aug. 31, 2010 [Inventor—Svensby; Applicant—Mölnlycke Health Care AB] [10 pages].
Applicant-Initiated Interview Summary issued on Nov. 28, 2012 for U.S. Appl. No. 12/671,781, filed Aug. 31, 2010 [Inventor—Svensby; Applicant—Mölnlycke Health Care AB] [3 pages].
Applicant-Initiated Interview Summary issued on Nov. 8, 2012 for U.S. Appl. No. 12/671,781, filed Aug. 31, 2010 [Inventor—Svensby; Applicant—Mölnlycke Health Care AB] [4 pages].
Final Rejection issued on Aug. 6, 2012 for U.S. Appl. No. 12/671,781, filed Aug. 31, 2010 [Inventor—Svensby; Applicant—Mölnlycke Health Care AB] [11 pages].
Response to Non-Final Rejection filed on May 7, 2012 for U.S. Appl. No. 12/671,781, filed Aug. 31, 2010 [Inventor—Svensby; Applicant—Mölnlycke Health Care AB] [12 pages].
Non-Final Rejection issued on Jan. 17, 2012 for U.S. Appl. No. 12/671,781, filed Aug. 31, 2010 [Inventor—Svensby; Applicant—Mölnlycke Health Care AB] [7 pages].
Preliminary Amendment filed on Feb. 2, 2010 for U.S. Appl. No. 12/671,781, filed Aug. 31, 2010 [Inventor—Svensby; Applicant—Mölnlycke Health Care AB] [8 pages].
Preliminary Amendment filed on Aug. 29, 2012 for U.S. Appl. No. 13/581,705, filed Aug. 29, 2012 [Inventor—Johannison; Applicant—Mölnlycke Health Care AB] [5 pages].

* cited by examiner

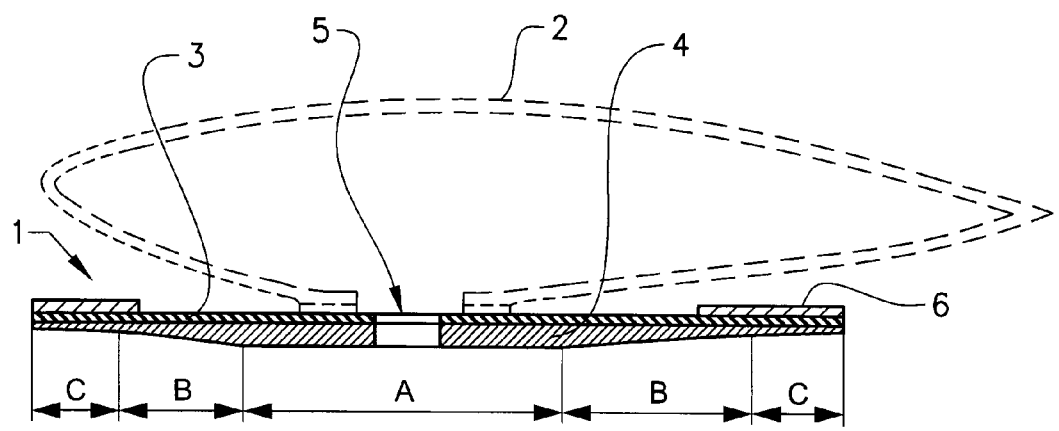

BODY ATTACHMENT WAFER FOR AN OSTOMY DEVICE

CROSS-REFERENCE TO RELATED APPLICATIONS

The present application is a U.S. National Phase Application of International Application No. PCT/SE2011/000067, filed Apr. 12, 2011, which claims priority to Swedish Patent Application No. 1050354-8, Apr. 12, 2010, and U.S. Patent Application No. 61/322,971, filed Apr. 12, 2010, all of which application are incorporated herein fully by this reference.

TECHNICAL FIELD

The present invention relates to a body attachment wafer for attaching an ostomy device to a wearer, comprising a plastic film having an opening therein, a layer of adhesive coated onto one side of said plastic film and a stiffening layer releasably attached to said plastic film on the side thereof opposite to the side coated with adhesive.

BACKGROUND OF THE INVENTION

An ostomy device is a device for storing body wastes of faeces and urine from a stoma, i.e. a terminal end of an intestine, extending from an artificial opening through the abdominal wall made by surgery. An ostomy device comprises a pouch and a body attachment wafer for attaching the pouch to the body of the wearer, the pouch and the body attachment wafer both having openings therein for accommodating the stoma.

The skin around the stoma is very sensitive and becomes easily irritated and infected if in contact with effluent from the stoma. It is therefore essential that such effluent is prevented from contacting the skin. There are several means known in prior art for preventing leaking of such effluent onto the skin surrounding the stoma. In U.S. Pat. Nos. 6,520,943 and 6,332,879, the body attachment wafer comprises a ring which fit snugly around the stoma and in U.S. Pat. No. 3,878,847 a thin elastic membrane extend over the stoma and assume the shape of the stoma. EP 1413268 discloses a ring adapter having a convex bodyside surface of a soft shape-recoverable material for use with a faceplate of an ostomy device. A hole in this adapter is given the shape of the individual stoma before application thereof. In order to prevent leaking of effluent onto the skin around the stoma such rings must be in contact with the stoma around the whole circumference thereof which can cause the stoma, which also is very sensitive, to be irritated. In WO 2006/075949 a separate ring or string of a carrier material enclosed on both sides by silicone adhesive is applied around the stoma for the protection of the sensitive skin around the stoma. Such a ring is effective but complicates the application of the ostomy device and may lead to a certain bulkiness.

The objective of the present invention is to ensure the protection of the skin around a stoma without making the manufacture of the ostomy device complex and without making the application thereof more complicated.

SUMMARY OF INVENTION

This objective is accomplished by a body attachment wafer for attaching an ostomy device to a wearer, comprising a plastic film having an opening therein, a layer of adhesive coated onto one side of said plastic film and a stiffening layer releasably attached to said plastic film on the side thereof opposite to the side coated with adhesive, characterized in that the layer of adhesive comprises a region surrounding the opening in the plastic film in which the thickness of the layer of adhesive is decreasing in a direction towards the circumference of the plastic film, the layer of adhesive having its largest thickness adjacent to the opening in the plastic film and consists of a silicone gel adhesive having a softness exceeding 8 mm. By having a region around the stoma which is thicker than in other regions it can be ensured that the adhesive will fill all irregularities in the skin around the stoma thereby ensuring that no effluent can leak, e.g. by capillary action, along such irregularities. Thereby the risk for local detachment of the body attachment wafer is also significantly reduced and the adherence force against skin of the adhesive will also be greater in such a region.

In a preferred embodiment said layer of silicone gel adhesive have a largest thickness of 0.1-10 mm, preferably 0.1-4 mm, more preferably 0.2-2 mm, and the minimum thickness of the layer of silicone gel adhesive is 0.05 mm.

Preferably, the layer of silicone gel adhesive has a region adjacent to the opening in the plastic film, in which the thickness of the layer of silicone gel adhesive does not decrease.

The layer of silicone gel adhesive can have an outermost region in which the layer of silicone gel adhesive has a minimum thickness.

BRIEF DESCRIPTION OF THE DRAWING

The invention will now be described with reference to FIG. 1, schematically showing a sectional view through a body attachment wafer according to a preferred embodiment of the invention.

DESCRIPTION OF EMBODIMENTS

FIG. 1 discloses a schematic sectional view of a body attachment wafer 1 according to a preferred embodiment of the present invention. A pouch 2 attached to the body attachment wafer 1 on the outer side thereof is outlined in interrupted lines.

The terms "outer" and "inner" refers to the location of the sides of the body attachment wafer 1 when it is applied to the wearer, the inner side being the side proximal to the skin of the wearer.

The body attachment wafer 1 consists of a thin plastic film 3 which on its inner side is coated with a layer 4 of adhesive and which have an opening 5 therein for accommodating a stoma. By having a thin plastic film it is ensured that body attachment wafer tightly can follow the surface of the skin when applied thereto. The plastic film 3 have a thickness of 100 micrometers or less, preferably 50 micrometers or less, more preferably 25 micrometers or less, and such a thin film is very difficult to handle. A stiffening layer in form of a frame 6 of a stiffening material extending in a region along the circumference of the plastic film 3 is releasably attached to the outer side thereof in order to facilitate application of the body attachment wafer. The frame 6 is removed from the plastic film 3 after or in connection with the application of the body attachment wafer.

As is conventional, a release layer (not shown) protects the layer 4 of adhesive during storing and transport of the body attachment wafer. This release layer is removed just before the application of the body attachment wafer.

The layer 4 of adhesive is thicker in a region A surrounding the opening 5 than in other regions. In region A, the layer 4 of adhesive has a constant thickness. In the preferred embodiment, the thickness of the adhesive layer 4 decreases in a region B surrounding region A in a direction towards the circumference of the plastic film 3 to a minimum thickness. In region C, surrounding region B, the layer 4 of adhesive has a constant minimum thickness.

It is hard to produce an adhesive layer having exact constant thickness with apparatus commonly used in manufacturing lines for ostomy devices. By the term "constant thickness" is in the present description and claims meant a thickness which is as constant as is possible with the application apparatus used in production lines for ostomy devices.

The layer 4 of adhesive shall consist of an adhesive having a softness exceeding 8 mm measured as a penetration value. The softness is measured by a method based on ASTM D 937 and described in WO2006/075950, which is referred to in this respect. A silicone gel adhesive is used. Such adhesives are skin friendly and have an excellent sealing effect. Examples of silicone gel adhesives suitable to be used as coating on the plastic film 3 are given in WO2006/075950, which is referred to in this respect.

Silicone gel adhesives with such softness have the ability to fill all irregularities in the skin provided that the thickness of the silicone gel adhesive is large enough. For this reason the layer 4 of silicone gel adhesive has a thickness in region A of 0.1-10 mm, preferably 0.1-4 mm and more preferably 0.2-2 mm. Thereby it is effectively ensured that effluent from the stoma can not flow between the skin and the adhesive layer 4 in cracks or the like in the skin. The sensitive skin in the region around the stoma will therefore be protected from the aggressive effluent from the stoma. It is also ensured that the risk of local detachment of a body attachment wafer 1 from the wearer due to effluent leaking in between the adhesive layer and the skin will be minimised.

The adherence force of the soft silicone gel adhesive against skin will also be increased in region A as compared to regions B and C. This is also an advantage since the pouch 2 is usually attached to the body attachment wafer 1 in this region A which means that loads from the pouch due to its weight (the weight of stored faeces and urine included) and external forces are transferred to the body attachment wafer 1 in this region and the load on the body attachment wafer will therefore be highest in this region.

The minimum thickness of the layer 4 of silicone gel adhesive in region C is preferably 0.05 mm in order to ensure a sufficient adherence force against skin for taking up the forces transferred from region A to this region (mainly as shear forces) and external forces acting on the body attachment wafer, for example clothing rubbing against the body attachment wafer.

Preferably, the decrease in thickness in region B is continuous in order to facilitate an application of the body attachment wafer 1 in which all portions of the body attachment wafer is pressed against and adhered to the skin during application thereof. Furthermore, the inclination of layer 4 of silicone gel adhesive in region B relative to in regions A and C should for the same reason preferably be small.

The plastic film 3 consists preferably of a film of polyurethane (PU) but other plastic materials, such as polyethylene (PE) and ethylene-vinyl acetate (EVA) can also be used.

The frame 6 of stiffening material can consist of paper or plastic, e.g. polyethylene.

The pouch 2 is of conventional design and construction and form per se no part in the present invention. The pouch can be integrated with the body attachment wafer or attached thereto in connection with the application of the ostomy device to a wearer. The entrance opening of the pouch is usually reinforced and should preferably be larger than the opening in the body attachment wafer in order to enable the cutting of said opening into a shape complementary to the shape of the stoma of the wearer. In this respect it is pointed out that the adaption of the shape of the opening in the body attachment wafer aims to allow the stoma to fit into this opening, preferably without contact with the body attachment wafer in order to avoid the stoma to be irritated. However, due to the softness of the adhesive and the thinness of the plastic film, the risk for the stoma to be irritated is low even if the body attachment wafer accidently would contact the stoma.

The body attachment wafer can be circular but other shapes, such as oval, triangular and even rectangular, are possible. The shapes of the regions A-C can follow the shape of the body attachment wafer, e.g having circumferences with the same shape as the circumference of the body attachment wafer. However, regions A and B can have other shapes than the body attachment wafer, for example being circular for an oval, triangular or rectangular body attachment wafer.

The body attachment wafer according to the described embodiment can be modified without leaving the scope of invention. For example, region B of the layer of soft silicone gel adhesive can be extended to the circumference of the body attachment wafer, in which case no region C would be present. It is also possible to let region B extend up to the opening in the plastic film, in which case region A would be deleted. It is also possible to have regions with decreasing thickness having different inclinations. It is however essential that, after application of the ostomy device, the region of the adhesive layer adjacent to the stoma has the largest thickness in order to minimise the risk for effluent from the stoma to leak in under the adhesive layer. The outer surface of the layer of silicone gel adhesive, i.e. the surface distal from the plastic film, can be curved in the transition areas between the different regions. The stiffening layer can, in case of a body attachment wafer being separate from the pouch of the ostomy device, extend over the whole of or a major portion of the plastic film. The scope of invention shall therefore not be limited by the described embodiment but only by the content of the enclosed patent claims.

The invention claimed is:

1. A body attachment wafer for attaching an ostomy device to a wearer, comprising:
    a plastic film having an opening therein,
    a layer of hydrophobic adhesive coated onto one side of said plastic film, and
    a stiffening layer releasably attached to said plastic film on the side thereof opposite to the side coated with the hydrophobic adhesive,
    wherein the layer of the hydrophobic adhesive is configured to adhere to skin and comprises a region surrounding the opening in the plastic film in which the thickness of the layer of adhesive is decreasing in a direction towards the circumference of the plastic film, the layer of adhesive having its largest thickness adjacent to the opening in the plastic film, and
    wherein the layer of the hydrophobic adhesive consists of a hydrophobic silicone gel adhesive having a softness exceeding 8 mm.

2. The body attachment wafer of claim 1, wherein the layer of hydrophobic silicone gel adhesive has a thickness adjacent to the opening in the plastic film of 0.1 mm to 10 mm.

3. The body attachment wafer of claim 2, wherein a minimum thickness of the layer of hydrophobic silicone gel adhesive is 0.05 mm.

4. The body attachment wafer of claim 1, wherein the layer of hydrophobic silicone gel adhesive has a region adjacent to the opening in the plastic film, in which the thickness of the layer of hydrophobic silicone gel adhesive does not decrease.

5. The body attachment wafer of claim 1, wherein the layer of hydrophobic silicone gel adhesive has an outermost region in which the layer of hydrophobic silicone gel adhesive has a minimum thickness.

6. The body attachment wafer of claim 5, wherein the minimum thickness of the hydrophobic silicone gel adhesive measured in the outermost region is 0.05 mm.

7. The body attachment wafer of claim 1, wherein the layer of hydrophobic silicone gel adhesive has a largest thickness adjacent to the opening in the plastic film of 0.1 mm to 4 mm.

8. The body attachment wafer of claim 1, wherein the layer of hydrophobic silicone gel adhesive has a largest thickness adjacent to the opening in the plastic film of 0.2 mm to 2 mm.

* * * * *